United States Patent
Gabbay et al.

(10) Patent No.: US 9,603,534 B2
(45) Date of Patent: Mar. 28, 2017

(54) METHOD AND SYSTEM FOR ESTIMATING MOMENTARY CARDIOVASCULAR PERFORMANCE RESERVE

(71) Applicant: CARDIO SCALE LTD., Ganey Tikva (IL)

(72) Inventors: Uri Gabbay, Ganey Tikva (IL); Ben Zion Bobrovsky, Beit Zayit (IL)

(73) Assignee: CARDIO SCALE LTD., Tikva (IL)

( * ) Notice: Subject to any disclaimer, the term of this patent is extended or adjusted under 35 U.S.C. 154(b) by 160 days.

(21) Appl. No.: 14/375,355

(22) PCT Filed: Jan. 31, 2013

(86) PCT No.: PCT/IL2013/050090
§ 371 (c)(1),
(2) Date: Jul. 29, 2014

(87) PCT Pub. No.: WO2013/121414
PCT Pub. Date: Aug. 22, 2013

(65) Prior Publication Data
US 2015/0005647 A1    Jan. 1, 2015

(30) Foreign Application Priority Data
Feb. 13, 2012  (IL) .......................... 218088

(51) Int. Cl.
*A61B 5/0205*   (2006.01)
*A61B 5/021*    (2006.01)
(Continued)

(52) U.S. Cl.
CPC .......... *A61B 5/0205* (2013.01); *A61B 5/0004* (2013.01); *A61B 5/021* (2013.01);
(Continued)

(58) Field of Classification Search
CPC .......................... A61B 5/02028; A61B 5/0205
See application file for complete search history.

(56) References Cited

U.S. PATENT DOCUMENTS

| 4,798,211 A | 1/1989 | Goor et al. |
| 5,178,151 A | 1/1993 | Sackner |

(Continued)

FOREIGN PATENT DOCUMENTS

| CN | 1034665 A | 8/1989 |
| CN | 1422137 A | 6/2003 |

(Continued)

OTHER PUBLICATIONS

Elkington et al, Introduction to Cardiovascular Physiology, 2009, Anaesthesia Tutorial of the Week, 125: 1-8.*

(Continued)

*Primary Examiner* — Jacqueline Cheng
*Assistant Examiner* — Angeline Premraj
(74) *Attorney, Agent, or Firm* — Kinney & Lange, P.A.

(57) ABSTRACT

The invention relates to a method for determining a cardiovascular performance reserve for each individual patient, comprising the steps of: a) receiving input physiological data from the patient for obtaining a parameter Z which is or approximates the product of the Stroke Volume (SV) by the Systemic Vascular Resistance (SVR); b) providing a value representing the Respiratory Rate (RR) of said patient, wherein the Respiratory Rate (RR) value is provided by measurements using dedicated device(s), calculations from the input physiological data or manually by using best estimate; c) providing anthropometric data of said patient for calculating the Body Surface Area (BSA) of said individual, wherein the anthropometric data includes at least body dimensions (such as height and weight) of said patient; d) calculating the Cardiovascular Reserve (CVR) by using said (Continued)

Z parameter and said RR according to following formula: CVR=(Z/RR); e) calculating a Cardiovascular Reserve Index (CVRI) by standardizing said CVR (by said BSA) and normalizing it to a scale of 1 according to the following formula: CVRI=CVR/(BSA*4); and outputting said Cardiovascular Reserve Index.

14 Claims, 15 Drawing Sheets

(51) Int. Cl.

| | | |
|---|---|---|
| A61B 5/0215 | (2006.01) | |
| A61B 5/024 | (2006.01) | |
| A61B 5/029 | (2006.01) | |
| A61B 5/107 | (2006.01) | |
| A61B 5/02 | (2006.01) | |
| A61B 5/00 | (2006.01) | |
| A61B 5/08 | (2006.01) | |
| A61B 5/113 | (2006.01) | |

(52) U.S. Cl.
CPC .......... *A61B 5/024* (2013.01); *A61B 5/02007* (2013.01); *A61B 5/029* (2013.01); *A61B 5/0215* (2013.01); *A61B 5/02028* (2013.01); *A61B 5/08* (2013.01); *A61B 5/107* (2013.01); *A61B 5/4842* (2013.01); *A61B 5/1135* (2013.01); *A61B 2505/01* (2013.01)

(56) References Cited

U.S. PATENT DOCUMENTS

| | | | |
|---|---|---|---|
| 5,469,859 | A | 11/1995 | Tsoglin et al. |
| 5,928,155 | A | 7/1999 | Eggers et al. |
| 7,054,679 | B2 | 5/2006 | Hirsh |
| 2003/0120164 | A1* | 6/2003 | Nielsen .............. A61B 5/02055 600/513 |
| 2004/0220637 | A1* | 11/2004 | Zdeblick ............ A61B 5/02028 607/17 |
| 2005/0090753 | A1 | 4/2005 | Goor et al. |
| 2006/0069535 | A1* | 3/2006 | Mnatsakanyan ...... G06F 19/345 703/2 |
| 2008/0001735 | A1 | 1/2008 | Tran |
| 2011/0152651 | A1 | 6/2011 | Berkow |

FOREIGN PATENT DOCUMENTS

| | | |
|---|---|---|
| WO | 9851211 A1 | 11/1998 |
| WO | 0167948 A2 | 9/2001 |
| WO | 02/078539 A1 | 10/2002 |
| WO | 02078539 A1 | 10/2002 |
| WO | 2010144961 A1 | 12/2010 |

OTHER PUBLICATIONS

AARC, Adult Mechanical Ventilator Protocols, 2003, Web, Retrieved from https://c.aarc.org/resources/protocol_resources/documents/general_vent.pdf.*
Medical Dictionary, Cardiac reserve | definition of cardiac reserve by Medical Dictionary, 2003, Web, Retrieved from http://medicaldictionary.thefreedictionary.com/cardiac+reserve.*
Lifeclinic, Why Does Exercise Lower BP?, 2002, Web, Retrieved from http://www.lifeclinic.com/focus/blood/articleView.asp?MessageID=1492.*
Weber et al, Oxygen Utilization and Ventilation During Exercise in Patients with Chronic Cardiac Failure, 1982, Circulation, 65(6): 1213-1223.*
Peabody, Cardiac Dyspnea, 1918, The American Journal of the Medical Sciences, 155: 114.*
Williams et al, Management of cardiogenic shock complicating acute myocardial infarction: towards evidence based medical practice, 2008, Heart, 83: 621-626.*
International Search Report for PCT/IL2013/050090, dated May 20, 2013.
International Preliminary Report on Patentability in PCT/IL2013/050090, dated May 14, 2014.
Hunt SA, Abraham WT, Chin MH et al., ACC/AHA 2005 Guideline Update for the Diagnosis and Management of Chronic Heart Failure in the Adult.
Antonelli M, Levy M, Andrews PJD et al., Hemodynamic monitoring in shock and implications for management, International Concensus Conference, Paris, France, Apr. 27-28, 2006, Intensive Care Medicine, 2006;4:575-590.
Serwin R, Audwin JG, Meena M. "Caring for critically ill patient in the emergency department", Emergency Medicine Reports, 2011; 32:193-207.
Allgöwer M, Buri C., "The "Shock Index"", Dtsch Med Wochenschr 1967; 92:1947-1950.
Olerud S. Allgöwer M., "Evaluation and management of the polytraumatized patient in various centers", World J. Surg. 1983; 7:143-148.
Williams SG, Cooke GA, Wright DJ, Parsons WJ, Riley RL, Marshall P, Tan LB., "Peak exercise cardiac power output; a direct indicator of cardiac function strongly predictive of prognosis in chronic heart failure", Eur Heart J. 2001; 22:1496-1503.
Packer M, Abraham WT, Mehra MR et-al., "Utility of impedance cardiography for the identification of short-term risk of clinical decompensation in stable patient with chronic heart failure", Journal of the American college of Cardiology, 2006; 47:2245-2252.
Malik M et-al., "Heart rate variability, standards of measurement, physiological interpretation, and clinical use", Task Force of the European Society of Cardiology, The North American Society of Pacing Electrocardiography.
Tarassenko L, Hann A, Young D. "Integrated monitoring and analysis for early warning of patient deterioration", British Journal of Anaesthesia. 2006;97:64-8.
Alarms in the intensive care unit: too much of a good thing is dangerous: is it time to add some intelligence to alarms? by Blum JM et. al., Crit Care Med. Feb. 2010; 38(2):451-6.
Imhoff M, Kuhls S, "Alarm algorithms in critical care monitoring", Anesth. Analg. 2006; 102:1525-37.
The criteria committee of the New York Heart Association, "Nomenclature and criteria for diagnosis of disease of the heart and great vessels", 9th edition, Boston, Mass: Little, Brown & Co; 1994:253-256.
Malpas SC, Neural influences on cardiovascular variability: possibilities and pitfalls in Am J Physiol Heart Circ Physiol. 2002;282:H6-H20.
Murray WB, Gorven AM, "Invasive v. non-invasive blood pressure measurements—the influence of the pressure contour", S. Afr. Med. J. 1991; 79: 134-9.
Darcy H. Les "Fontaine publiques de la ville de Dijon", Dalmont, Paris. 1856.
Mosteller RD, "Simplified calculation of body surface area", N. Engl. J. Med. 1987; 317:1098.
Kleiger RE, Miller JP, Bigger JT, Moss AJ, "Decreased heart rate variability and its association with increased mortality after acute myocardial infarction" Am. J. Cardiol. 1987; 59:256-62.
Gabbay U, Bobrovsky BZ, "Hypothesis: Low frequency heart rate variability (LF-HRV) is an input for undisclosed yet biological adaptive control, governing the cardiovascular regulations to assure optimal functioning", Medical Hypotheses. 2012;78:211-12.
Receiver Operating Characteristics curves and related decision measures: a tutorial, Chemometrics and Intelligent Laboratory Systems, 2006; 80:24-38.
Supplementary Search Report and Written Opinion, from EP Application Serial No. 13749270.8.
Irene Alyn et al., Cardiovascular anatomy and physiology of the fetus, neonate, infant, child, and adolescent,J Cardiovasc Nurs, vol. 6, No. 3, Jan. 1992.

(56) References Cited

OTHER PUBLICATIONS

Hariharan S et al., Risk Scoring in Perioperative and Surgical Intensive Care Patients: A Review, Current Surgery, Wiliams and Wilkins, Baltimore, US, vol. 63, No. 3, May 1, 2006.
English translation of Chinese Office Action dated Nov. 11, 2015, received for corresponding Chinese Application No. 201380009232.7.
Japanese Office Action, for Japanese Patent Application No: 2014-556194, dated Dec. 2, 2016, 6 pages.

* cited by examiner

METHOD AND SYSTEM FOR ESTIMATING MOMENTARY CARDIOVASCULAR PERFORMANCE RESERVE

FIELD OF THE INVENTION

The present invention relates to the field of medical diagnostic. More particularly, the invention relates to a method utilizing either invasive measurements or non invasive vital signs to estimate quantitatively cardiovascular performance reserve, to indicate (through the cardiovascular reserve measure) the cardiovascular status in general and to predict the diagnosis (e.g. shock or heart failure) and evaluate its course.

BACKGROUND OF THE INVENTION

At present two major cardiovascular related morbidities, namely (a) heart failure and (b) shock (of all kinds) are lacking measurable indicator, diagnostic test, monitoring and follow-up capabilities (see a report of the American College of Cardiology/American Heart Association Task Force, Task Force on Practice Guidelines by Hunt S A, Abraham W T, Chin M H et al. "ACC/AHA 2005 Guideline Update for the Diagnosis and Management of Chronic Heart Failure in the Adult", and the publication by Antonelli M, Levy M, Andrews P J D et al. "Hemodynamic monitoring in shock and implications for management", International Concensus Conference, Paris, France, 27-28 Apr. 2006, Intensive Care Medicine, 2006; 4:575-590) wherein:

Heart failure refers herein to a global term for the physiological state (either an acute event or chronic course) in which cardiac output is insufficient in meeting the needs of the body (manifested as intolerability to perform different levels of physical activity). It is usually due to cardiac dysfunction (low cardiac output heart failure) but may also occur when the body's requirements for oxygen and nutrients are increased and the demand outstrips what the circulation can provide (e.g. severe anemia, Gram negative septicemia, beriberi, thyrotoxicosis, Paget's disease, arteriovenous fistulae, etc. (termed "high output cardiac failure"); and Shock (also known as circulatory shock) refers herein to a life threatening condition of acute circulatory failure characterized by inadequate or inappropriately distributed tissue perfusion, which results in generalized cellular hypoxia. There are several shock types characterized by the underlying mechanisms (cardiogenic, hypovolemic, obstructive and distributive, etc.). However, regardless the underlying cause, all types of shock share identical manifestation of tissue level perfusion insufficiency. The mortality rate is very high and reaches 50%. All types of shock lack a satisfactory single diagnostic test or quantitative measure to evaluate the proceedings leading to shock and recognized pending or pre shock condition. In shock, either Cardiac Output (CO) or Systemic Vascular Resistance SVR (also known as total peripheral resistance) or both are severely decreased (see Serwin R, Audwin J G, Meena M. "Caring for critically ill patient in the emergency department", Emergency Medicine Reports, 2011; 32:193-207).

Existing Diagnostic Methods

Early diagnosis is essential in order to intervene before irreversible consequences occur. Diagnosis is clinical and no specific test is available (see Serwin R, Audwin J G, Meena M. "Caring for Critically Ill Patient in the Emergency Department", Emergency Medicine Reports, 2011; 32:193-207). Low blood pressure is not synonym to shock nor tachycardia. Shock Index (SI) which is the quotient of Systolic Blood Pressure (SBP) by Heart Rate (HR): SI=SBP/HR, was first introduced in 1967 (by Allgöwer M, Burri C., "The "Shock Index"", Dtsch Med Wochenschr 1967; 92:1947-1950) but was not implemented as a standard of evaluation and is still controversial (see Olerud S. Allgöwer M., "Evaluation and management of the polytraumatized patient in various centers", World J. Surg. 1983; 7:143-148).

Invasive hemodynamic measurements are carried out in order to provide a diagnostic basis of the cardiovascular performance (see for example, Williams S G, Cooke G A, Wright D J, Parsons W J, Riley R L, Marshall P, Tan L B., "Peak exercise cardiac power output; a direct indicator of cardiac function strongly predictive of prognosis in chronic heart failure", Eur Heart J. 2001; 22: 1496-1503) but are complicated costly and risky.

Furthermore, even when invasive measurements were taken the insight was neither satisfactory nor conclusive in cases of heart failure or shock (see Hunt S A, Abraham W T, Chin M H et al., "ACC/AHA 2005 Guideline Update for the Diagnosis and Management of Chronic Heart Failure in the Adult: a report of the American College of Cardiology/American Heart Association Task Force, Task Force on Practice Guidelines", and Antonelli M, Levy M, Andrews P J D et-al., "Hemodynamic monitoring in shock and implications for management", International Concensus Conference, Paris, France, 27-28 Apr. 2006, Intensive care Medicine, 2006; 4:575-590). Even cardiac output which is considered the most significant cardiovascular measure fails to predict accurately shock and heart failure (Antonelli M, Levy M, Andrews P J D et-al., "Hemodynamic monitoring in shock and implications for management", International Concensus Conference, Paris, France, 27-28 Apr. 2006, Intensive care Medicine, 2006; 4:575-590).

In order to avoid invasive hemodynamic measurements on one hand and in order to provide hemodynamic information on the other hand, several indirect methods were suggested, for example, such as those disclosed in US Patent applications No. 2011/0152651 and 2005/0090753A1, U.S. Pat. No. 4,798,211, U.S. Pat. No. 5,178,151, and U.S. Pat. No. 7,054,679 among which, suggestions included measurements of heart rate variability through ECG, impedance cardiography, movement and acceleration measurements and analysis of the pulse pressure shape through dedicated equipment. However, as for today none of such methods became significant in the clinical practice. As of the impedance cardiography method for example (Packer M, Abraham W T, Mehra M R et-al., "Utility of impedance cardiography for the identification of short-term risk of clinical decompensation in stable patient with chronic heart failure", Journal of the American college of Cardiology, 2006; 47:2245-2252) it remains in the research arena. As for heart rate variability (HRV) for example (Malik M et-al., "Heart rate variability, standards of measurement, physiological interpretation, and clinical use", Task Force of the European Society of Cardiology, The North American Society of Pacing Electrocardiography) only seldom it is still used to predict myocardial infarction prognosis.

Acute phase monitoring systems of the severely ill patient (such as in intensive care or intermediate) are based on vital signs which induce an alarm which can be schematically classified into four main categories: 1. out of range of a single vital sign, 2. trend evaluation of a single vital sign, 3. wave related analysis (e.g. ECG, blood pressure or respiration), and 4. complex algorithms that involve multiple vital signs formulas predicting specific or non specific deterioration or negative outcome (Tarassenko L, Hann A, Young D. "Integrated monitoring and analysis for early warning of patient deterioration", British Journal of Anaesthesia. 2006; 97:64-8). Several publications complaint that though alarm algorithm may accurately predict deterioration, it lacks in providing intelligence (Bloom J, Tremper K K, "Alarm in the intensive care unit: too much of a good thing is dangerous: is it time to add some intelligence to alarms?" Crit. Care Med., 2010; 38:702-703). Hence, alarm should include two characteristics: first, being accurate alarm validly predicting or detecting deterioration or negative outcome, the second (nevertheless important) is providing intelligence or insight either pointing toward a specific impairment or directing the staff towards the appropriate response. Most of the comprehensive alarms were proven accurate in prediction of deterioration, but lacked in pointing toward the underlying impairment hence left the staff unknowing where the impairment were exactly located. Unfortunately, this result sometimes in turning the alarm off by the frustrated staff (Bloom J, Tremper K K, "Alarm in the intensive care unit: too much of a good thing is dangerous: is it time to add some intelligence to alarms?" Crit. Care Med., 2010; 38:702-703, and Imhoff M, Kuhls S, "Alarm algorithms in critical care monitoring", Anesth. Analg. 2006; 102:1525-37).

Therefore, it is an object of the present invention to provide a system which is capable to estimate the cardiovascular performance reserve (which is defined later) through either invasive measurements or non invasive vital signs, and by which to indicate the cardiovascular status of a patient.

It is another object of the present invention to provide a single diagnostic test to quantitatively diagnose heart failure, to quantify its severity and to monitor severity dynamic in the short term and to follow changes of the long term.

It is yet another object of the present invention to provide a single diagnostic test to quantitatively diagnose shock and to quantify its severity and to monitor severity dynamic.

It is still another object of the present invention to provide an alarm system which is capable to estimate the cardiovascular performance reserve, through invasive measurement or non-invasive vital signs, and by which to indicates the cardiovascular status of a patient and as derived by this status to alarm while detecting cardiovascular deterioration, indication or prediction.

Other objects and advantages of the invention will become apparent as the description proceeds.

SUMMARY OF THE INVENTION

The invention relates to a method for determining a cardiovascular performance reserve for each individual patient, comprising the steps of:
a. receiving input physiological data from the patient for obtaining a parameter Z which is or approximates the product of the Stroke Volume (SV) by the Systemic Vascular Resistance (SVR);
b. providing a value representing the Respiratory Rate (RR) of said patient, wherein the Respiratory Rate (RR) value is provided by measurements using dedicated device(s), calculations from the input physiological data or manually by using best estimate;
c. providing anthropometric data of said patient for calculating the Body Surface Area (BSA) of said individual, wherein the anthropometric data includes at least body dimensions (such as height and weight) of said patient;
d. calculating the Cardiovascular Reserve (CVR) by using said Z parameter and said RR according to following formula:

$$CVR=(Z/RR);$$

e. calculating a Cardiovascular Reserve Index (CVRI) by standardizing said CVR (by said BSA) and normalizing it to a scale of 1 according to the following formula:

$$CVRI=CVR/(BSA*4);$$ and f. outputting said Cardiovascular Reserve Index.

According to an embodiment of the present invention, the input physiological data are measurable hemodynamic-related data of the patient which yield the actual SV and SVR of said patient (i.e., Z=SV*SVR).

According to an embodiment of the present invention, Z is approximated by the formula Z=80*(MABP−CVP)/HR, wherein the input physiological data are measurable either from non invasive vital signs measurements or, if available, from an invasive measurements through an arterial catheter and wherein said measurable data is used for obtaining the Mean Arterial Blood Pressure (MABP), the Heart Rate (HR), and if available, the Central Venous Pressure (CVP) of said patient. According to an embodiment of the invention, the cardiovascular reserve index can be calculated by using the difference (MABP−CVP) or the difference best estimate if CVP is not available.

According to embodiments of the invention, the method further comprises providing indication on cardiovascular status at a specific time point for diagnostic purposes determining whether medical decision making is required for the individual based on the outputted index and the said indication. The method may further comprise providing indication on cardiovascular status by trend over time for cardiovascular dynamics indication, determining whether medical attention is required for the individual based on the outputted index and the said indication (e.g., for decision making). Wherein for both cases, the method may further used for prioritizing medical assistance for the individual based on the cardiovascular reserve index and indication as compared to indices and indications of other individuals awaiting medical assistance or triage.

According to embodiments of the invention, outputting the cardiovascular reserve index includes displaying the index for at least one individual, and creating a graph consisting of the current index and a plurality of past indexes for said individual with or without indication on the trend over time (such as "stable" "deterioration" or "improvement", etc).

In another aspect the invention relates to a system for estimating momentary cardiovascular reserve, comprising:
a) at least one data source capable of being connected to at least one individual for obtaining physiological data from said individual and for obtaining anthropometric data related to each individual; and
b) an analysis unit in communication with said data source for possessing the data received from said data source, in order to determine an index representing said momentary cardiovascular reserve index.

According to an embodiment of the present invention, the data source includes a vital sign monitor (or sensor(s)), wherein said vital sign monitor will be in communication with the individual where in communication includes having said vital sign monitor affixed, attached, implanted, coupled, abutting the individual's tissue, resident in clothing or equipment worn by said individual, and/or proximate to said individual. According to some embodiments of the invention, the data source is connected to a transmitter (and/or receiver) that allows physiological data and anthropometric data to be communicated to the analysis unit, thereby allowing remote monitoring of the individual or monitoring during a medical event such as triage, transport, treatment or telemedicine decision.

According to an embodiment of the present invention, the analysis unit is in communication with the data source through a wired connection and/or wireless connection. Optionally, the analysis unit can be a separate component not present on the individual on whom the data source is present or in communication with.

DETAILED DESCRIPTION OF THE INVENTION

Figure 1:
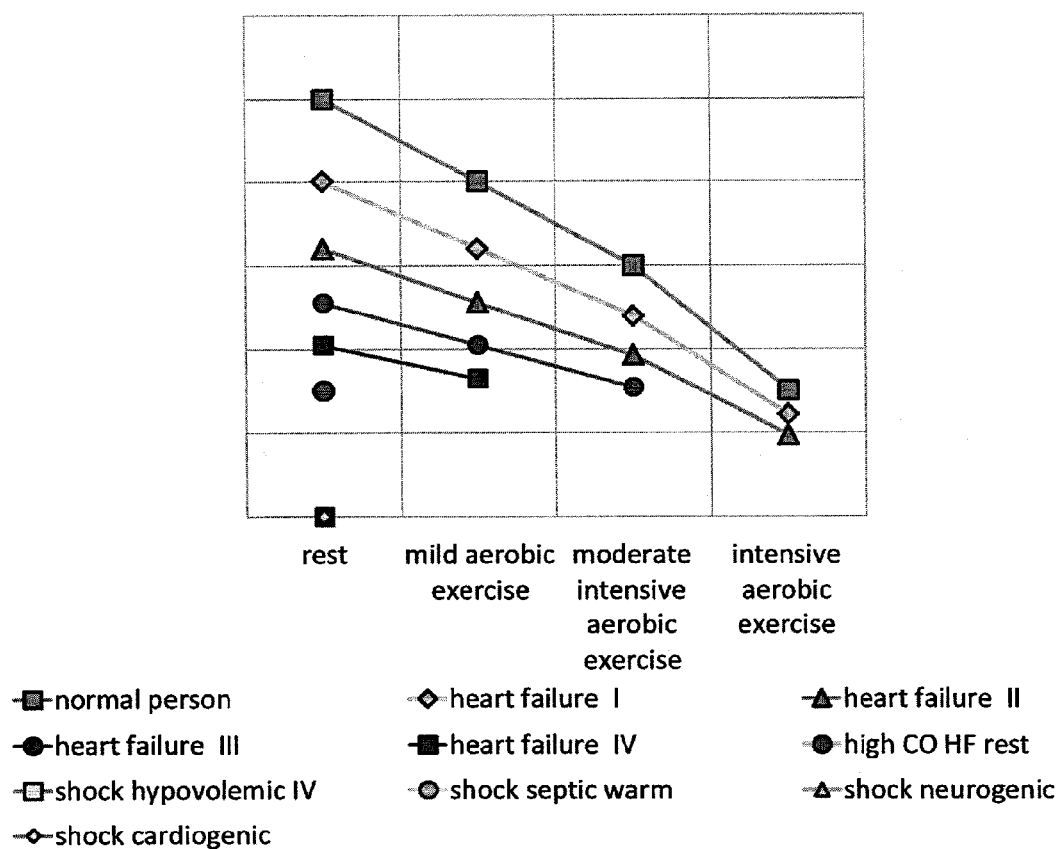
FIG. 1 describes the conceptual (hypothetical) cardiovascular reserve dependency by physical activity intensity and by heart failure severity.

The present invention relates to a method and system for quantitatively estimating the cardiovascular performance reserve of a patient, a method to measure it, according which it may indicate the cardiovascular performance status and predict the cardiovascular performance related diagnosis.

The invention in at least one exemplary embodiment includes a device and method capable of calculating in real time a Cardio-Vascular Reserve Index (CVRI) which indicates quantitatively how much cardio-vascular performance reserve is left to an individual subject at the exact moment and condition of measurement—either at rest or under enhance physical activity or under any provocative intervention or during a disease or other medical condition. This allows gaining more timely information indicating the patient's cardiovascular performance reserve condition. The CVRI can also provide a trend indication whether an individual is improved, deteriorated or even approaching a cardiovascular collapse (shock).

The present invention is adaptable for use by medical emergency personnel or medics in any setting, such as road accident, disaster sites, combat zones, caregiver office, sport medicine or hospitals.

The systems and methods of the present invention allow better, simpler, immediate and more accurate evaluation and diagnosis of any of the above mentioned settings.

The systems and methods of the present invention also enable decision making support by health care providers confronting mass casualty event, regarding triage, namely which patient to treat or to evacuate earlier than the others.

An additional advantage provided by the invention is the real time displaying and documenting the CVRI of a patient or of a plurality of patients. This is important in many cases inasmuch as there is a plurality of injured patients, rendering it difficult for the medical crew to determine which patient they should treated earlier.

The figures and the following description relate to embodiments of the present invention by way of illustration only. It should be noted that from the following discussion, alternative embodiments of the structures and methods disclosed herein will be readily recognized as viable alternatives that may be employed without departing from the principles of the claimed invention.

Cardiovascular reserve is a term frequently used but the meaning was inconclusive. The embodiments of the present invention provides a novel cardiovascular paradigm according which healthy subjects, heart failure patients of diverse severities and shock of different types represent different placing along the cardiovascular performance reserve scale.

The method of the present invention is based on our conceptual insight of what cardiovascular performance related morbidities are. The underlying assumption is that the cardiovascular reserve at rest of a healthy subject is maximal. Heart failure patient may have reduced cardiovascular reserve at rest (proportional to the heart failure severity). Each subject at rest can perform physical activity and may increase it until reaching cardiovascular exhaustion.

Exhaustion is, according our paradigm, a reversible debilitating condition that disabled further increase or even maintaining the present physical activity level.

Healthy subject reaches that exhaustion level only following intensive physical activity while heart failure patient will reach exhaustion level at milder efforts which we may refer to as premature cardiovascular exhaustion. In order to determine the best course of therapy, physicians often assess the stage of heart failure according to the New York Heart Association (NYHA) functional classification system (The criteria committee of the New York Heart Association, "Nomenclature and criteria for diagnosis of disease of the heart and great vessels", 9th edition, Boston, Mass.: Little, Brown & Co; 1994:253-256). This classification relates symptoms to the patient capability to perform everyday activities (i.e. based on the patient anamnesis). We expect heart failure patient NYHA Class I to be capable of performing considerable effort very closed to healthy subject before reaching exhaustion, while NYHA Class IV patient is expected to be capable to perform only mild exercise before reaching exhaustion. In general we refer to "heart failure" as "reduced cardiovascular performance reserve" proportional to the severity of heart failure which reaches exhaustion earlier (premature exhaustion).

Under the same conceptual assumption the term "shock" with respect to the cardiovascular performance reserve is further deterioration on the cardiovascular reserve scale which had reached cardiovascular insufficiency. Shock is an unsustainable condition, non reversible spontaneously, i.e. unless intervene to correct would undergo a devastating chain of events until death.

We assumed that each of these conditions can be placed in ordinal order on the cardiovascular performance reserve scale. FIG. 1 presents graphically the dependence of the expected cardiovascular performance reserve on heart failure severity and exercise intensity according our conceptual hypothesis. The graphical expression of the conceptual hypothesis of cardiovascular performance reserve resembles low frequency heart rate variability (LF-HRV) power decrease on physical activity and with morbidity (heart failure) [Malpas S C, Neural influences on cardiovascular variability: possibilities and pitfalls in Am J Physiol Heart Circ Physiol. 2002; 282:H6-H20]. The overall principle can be summarized as the severer the morbidity the lower the cardiovascular reserve and the intensified the physical activity the lower the cardiovascular reserve left.

We assume that given our conceptual hypothesis is true, then there must be an underlying measurable hemodynamic characteristic or parameter which its respective values place these conditions accordingly on the cardiovascular performance reserve scale as the conceptual hypothesis had predicted.

Before further describing our work we recall some relevant hydrodynamic variables, their definitions and relationships which are already known:

CO [cm³/min]—Cardiac Output
SV [cm³]—Stroke Volume
HR [beat/min]—Heart Rate
RR [respirations/min]—Respiratory Rate
SVR [dynes*sec$^{-1}$*cm$^{-5}$]—Systemic Vascular Resistance (also known as TPR Total Peripheral Resistance)
SBP [mmHg]—Systolic Blood Pressure
DBP [mmHg]—Diastolic Blood Pressure
RAP [mmHg]—Right Atrial Pressure
CVP [mmHg]—Central Vein Pressure (which is considered as approximation of RAP]
MABP [mmHg]—Mean Arterial Blood Pressure MABP should be calculated by:

$$\int_0^T p(t)dt/T$$

in which p(t) is the instantaneous actual arterial blood pressure as measured in invasive blood pressure measurements, dynamically ranges between SBP and DBP, and T is the time span.

Simpler estimates of MABP may be used as regard with non-invasive blood pressure measurements. It is common to assume that MABP is approximated by the following formula:

(1) MABP≈DBP+(SBP−DBP)/3 (see Cardiovascular Physiology Concept. Editor Klabunde R E, Second Edition, Lippincott Williams & Wilkins, 2011)

It should be noted that MABP approximation depends on the pulse pressure curve shape and on heart rate (see Murray W B, Gorven A M, "Invasive v. non-invasive blood pressure measurements—the influence of the pressure contour", S. Afr. Med. J. 1991; 79: 134-9) so the approximation of MABP in formula (1) may be deviated.

Some relationships between the hemodynamic parameters are already known based on physical principles. By simplifying Darcy's Law (Darcy H. Les "Fontaine publiques de la ville de Dijon", Dalmont, Paris. 1856), we get the equation:

Flow=Pressure difference/Resistance

When applied to the circulatory system, we get:

$CO=80\times(MABP-RAP)/SVR$ (2)

CO can be also given by:

$CO=SV*HR => SV=CO/HR$ (3)

BSA [m²]—Body Surface Area

There are several approximate expressions of BSA, for example Mosteller formula (Mosteller R D, "Simplified calculation of body surface area", N. Engl. J. Med. 1987; 317:1098):

$BSA=(weight(kg)*Height(cm)/3600)^{0.5}$ (4)

It is a common practice to normalize some of the hemodynamic parameters by BSA.

In order to identify the above mention underlying parameter according to our conceptual hypothesis we had allocated the specific hemodynamic parameter representative/average value for a diversity of conditions (such as healthy subject at rest, heart failure patients of different severity levels, different levels of exercise of healthy subjects and heart failure patients, as well as different types of shock).

We evaluated each of the hemodynamic parameters' capability to discriminate and organized the conditions on ordinal order (by morbidity level and physical activity intensity as predicted) by which, at rest, healthy subject is placed on one end and shock on the other hand (as shock patient can be considered incapable of exercise). As for exercise, healthy subject is placed on one end and the severer heart failure on the other end. Moreover we expect ordinal decrease by exercise intensity.

Figure 2:
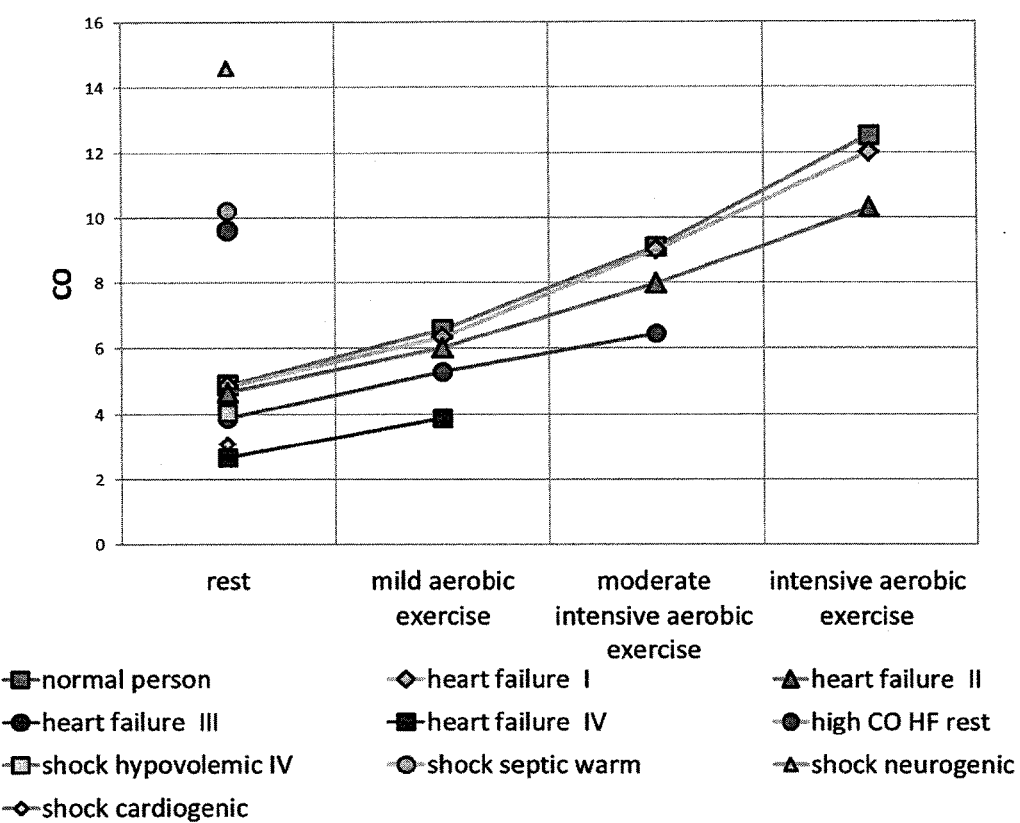
FIG. 2 describes Cardiac Output (CO) dependency by physical activity intensity and by heart failure severity putting the respective CO averages of each condition. As evident CO presents non-monotonously dependency, hence, CO cannot represent cardiovascular performance reserve.

We evaluated each hemodynamic parameter in order to realize whether it can solely places the above mention conditions on the cardiovascular reserve scale according our conceptual hypothesis. Some of which are for example CO and EF which frequently considered predictive to cardiovascular performance:

Cardiac Output (CO):

FIG. 2 presents Cardiac Output (CO) dependency by physical activity intensity and by heart failure severity. As can be clearly evident CO failed to play the role of cardiovascular performance reserve measure since it failed to discriminate and place the different conditions in ordinal order as expected by the conceptual hypothesis.

Figure 3:
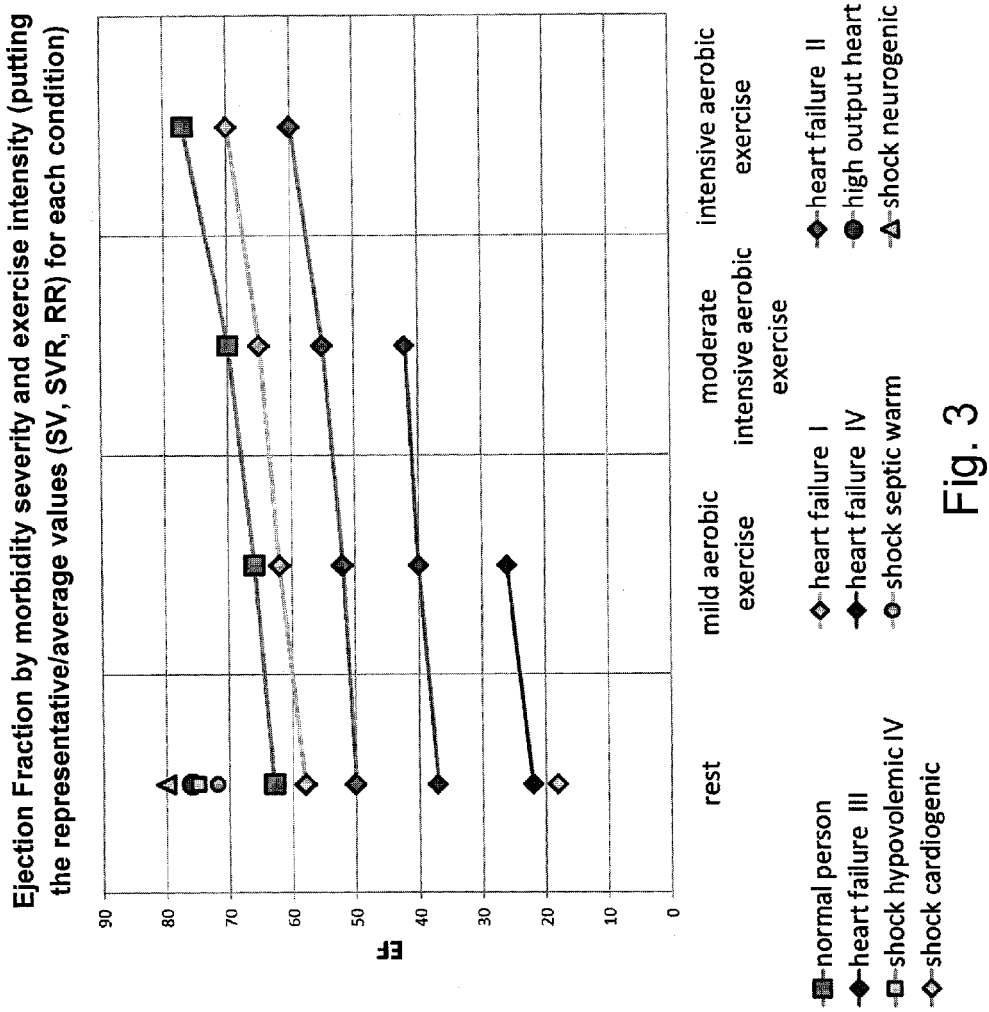
FIG. 3 describes Ejection Fraction (EF) dependency by physical activity intensity and by heart failure severity putting the respective EF averages of each condition. As evident EF presents non-monotonously dependency hence EF cannot represent cardiovascular performance reserve.

Ejection Fraction (EF):

FIG. 3 presents Ejection Fraction (EF) dependency by physical activity intensity and by heart failure severity. As can be clearly evident EF failed to play the role of cardiovascular reserve measure since it failed to discriminate and place the different conditions in ordinal order.

As neither of the individual hemodynamic parameters complied with our cardiovascular reserve hypothesis we analyzed the combination of hemodynamic parameters.

Reference will now be made to several embodiments of the present invention, examples of which are illustrated in the accompanying figures. Wherever practicable similar or like reference numbers may be used in the figures and may indicate similar or like functionality. The figures depict embodiments of the present invention or show relevant graphs for purposes of illustration only. One skilled in the art will readily recognize from the following description that alternative embodiments of the structures and methods illustrated herein may be employed without departing from the principles of the invention described herein.

Figure 4:
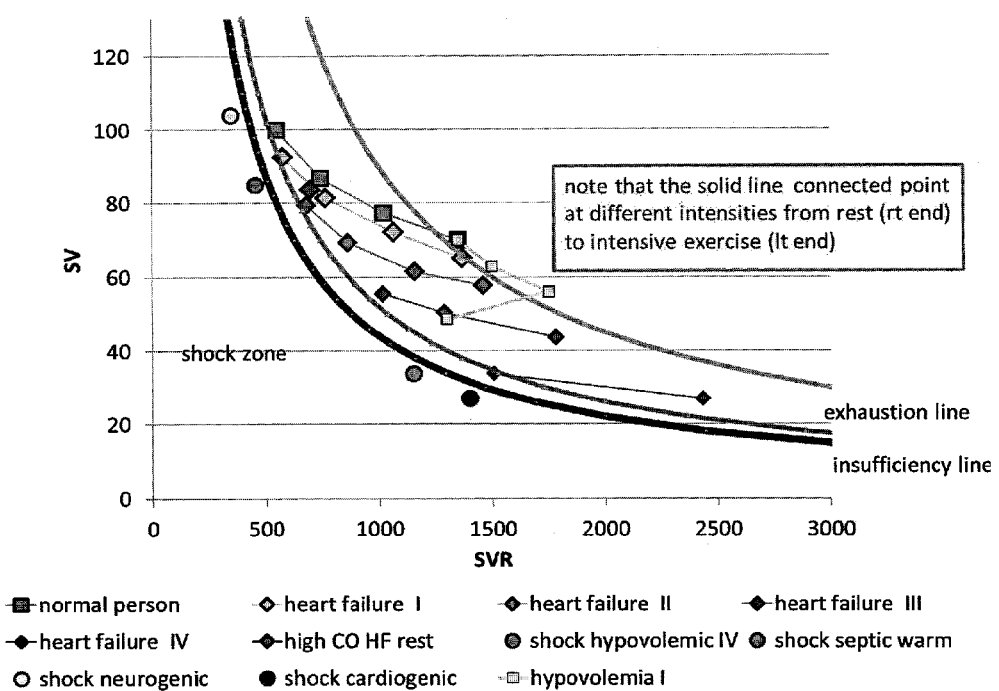
FIG. 4 describes the dependency of different conditions on SV (as Y axis) and SVR (as X axis), and demonstrates various hyperbolic iso-product curves (each hyperbolic line represent a constant product of SV×SVR)

While plotting the different conditions according their representative SV values on Y axis and their representative SVR values on X axis, we had realized that the different types of shock were located differently though not randomly, but rather draw a hyperbolic like curve (as shown in FIG. 4). Taking the insight of the hyperbolic curves further we realized that the product SV*SVR defined various hyperbolic iso-product (i.e. SV*SVR) curves. At rest a healthy subject is on the highest iso-product curve and all types of shock are on different locations on the lowest. While exercising a healthy subject moves from right to left and accordingly from a higher iso-product curve to a lower one. A heart failure patient at rest is already on a lower iso-product curve (lower than the healthy one) and he moves further to a lower iso-product curve while exercising. The intensified the exercise, the lower the placing on a SV*SVR iso-product curve until reaching an exhaustion's curve. A heart failure patient that is anyhow on a lower iso-product curve at rest reaches exhaustion curve earlier (premature exhaustion) following milder physical activity intensity (which is reciprocal to his heart failure severity). However the exhaustion curve is identical to all conditions.

Hence, we had concluded that the cardiovascular reserve measure may be proportional to the product of both SV×SVR. Interestingly this product (SV×SVR) is proportional to the "open loop gain" of the baro-receptor control loop model (Dvir H, Bobrovsky B Z, Gabbay U. "A novel heart rate control model provides insights linking LF-HRV behavior to the open loop gain components". Accepted for publication by IJC). The decisive role of the "open loop gain" on the mechanism and behavior of the low frequency heart rate variability (LF-HRV) was also pointed out there, showing that high open loop gain results in high LF-HRV power. Since LF-HRV power is believed to be associated with favored prognosis and vise versa, lack of LF-HRV at rest predicts bad prognosis (Kleiger R E, Miller J P, Bigger J T, Moss A J, "Decreased heart rate variability and its association with increased mortality after acute myocardial infarction" Am. J. Cardiol. 1987; 59:256-62). The importance of the open loop gain in the cardiovascular performance was further discussed in (Gabbay U, Bobrovsky B Z, "Hypothesis: Low frequency heart rate variability (LF-HRV) is an input for undisclosed yet biological adaptive control, governing the cardiovascular regulations to assure optimal functioning", Medical Hypotheses. 2012; 78:211-12).

Figure 5:
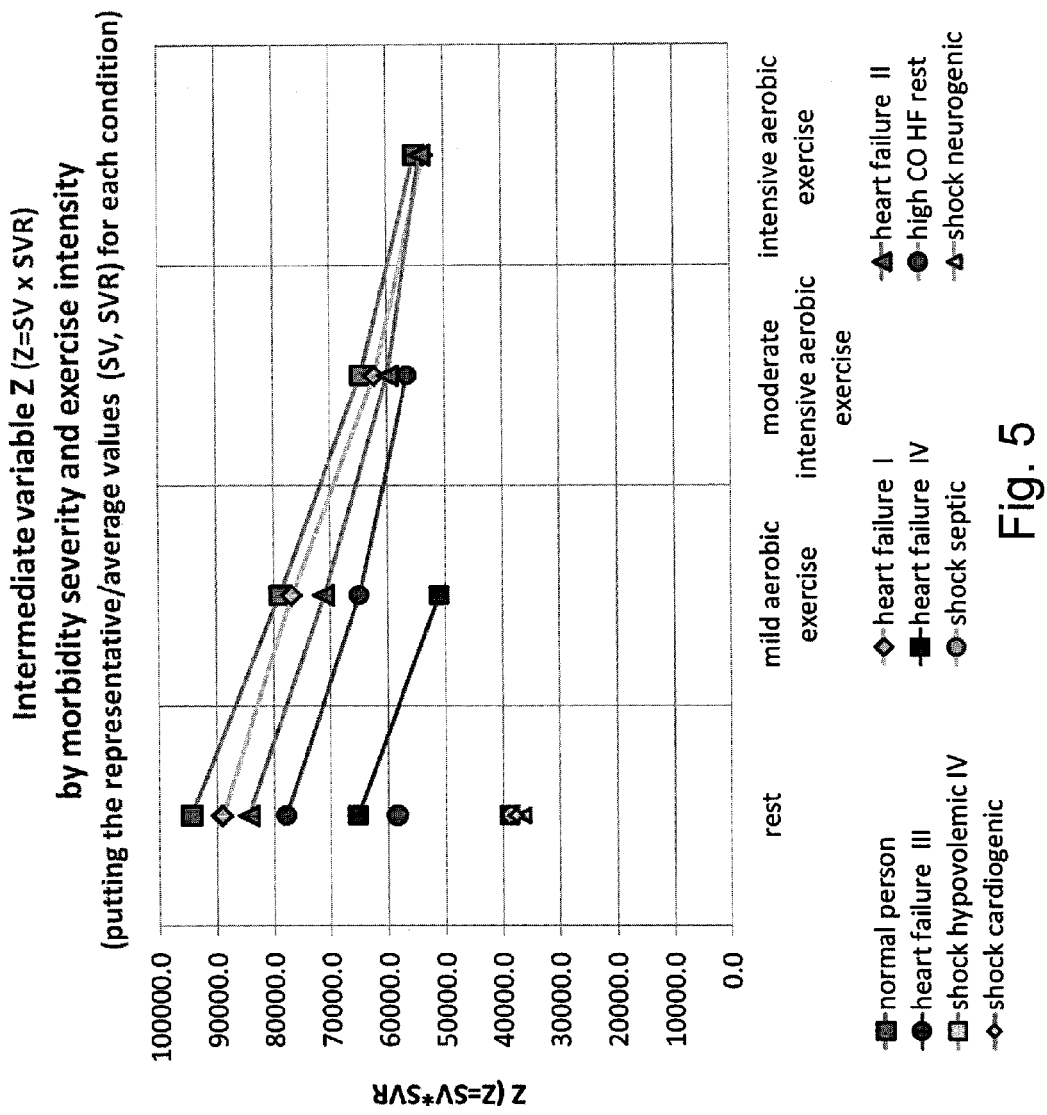
FIG. 5 describes intermediate variable Z (which is the product of SV by SVR) dependency by physical activity intensity and by heart failure severity, putting the respective SV and SVR averages and calculating Z for each condition. As evident Z presents monotonously dependence, hence, Z can represent cardiovascular reserve.

An intermediate parameter Z which is the product of SV by SVR (Z=SV*SVR), is presented in FIG. 5 presenting Z dependency by physical activity intensity and by heart failure severity. Z may play the role of cardiovascular performance reserve measure since it discriminate and place the different conditions in ordinal order as had been predicted by the conceptual hypothesis in FIG. 1. At rest normal subject is on one end and shock on the other end. In exercise of whatever intensity a healthy subject is on one end and heart failure on the other end. Moreover the changes with exercise intensity are according to the expected.

Following empirical and statistical experiments we found that the cardiovascular performance reserve is best discriminated when Z (the product of SV and SVR) was also divided by respiratory rate (RR). Cardiovascular Reserve (none standardized) CVR is given by:

$$CVR=Z/RR=(SV*SVR)/RR \quad (5)$$

While evaluating heterogeneous population, even better discrimination is gained by Standardized CVR by dividing CVR by BSA and in order to normalize the measure to a scale of 1 by further dividing by 4 (empirically) to obtain CVRI—cardiovascular reserve index as given by:

$$CVRI=CVR/(BSA*4)=Z/(RR*BSA*4)=SV*SVR/(RR*BSA*4) \quad (6)$$

If the measurement of SV and SVR are known, then formula (6) may be the bottom-line formula.

In most cases both SV and SVR measurements are unfeasible. However, even though each of the parameters (SV and SVR) is very difficult to be measured, we found that the product (SV*SVR) can be calculated by using alternative parameters, thus the product SV*SVR (i.e., the intermediate parameter Z) can be obtained and replaced by the formula [Z=80*(MABP−CVP)/HR], as will be further explained hereinafter.

All the above will be better understood through the following illustrative and non-limitative description and examples. For the sake of brevity, however, the CVRI calculations that were found to yield the best results and examples will be described hereinafter.

The following is an exemplary method for determining an index for a patient according to an embodiment of the present invention. The method begins by receiving (or recording depending upon the implementation) the data from an individual that are required to obtain the following parameters: the Mean Arterial Blood Pressure (MABP), HR, RR and BSA. The data from the individual can be measured or obtained by different types of existing healthcare medical devices, or alternatively by a dedicated device configured to measure such data and accordingly to calculate CRVI as described in further details hereinafter.

Substitute SV in formula (5) using formula (3) and substitute SVR in formula (5) using formula (6), we get:

$$CVRI = 80*(MABP-CVP)/(RR*HR*BSA*4) \quad (7)$$
$$= 20*(MABP-CVP)/(RR*HR*BSA)$$

In case of intensive care patient or any patient with both arterial line and CVP line which measure directly arterial pressure and central vein pressure respectively, then (7) may be the bottom line formula.

The CVRI calculations employ the CVP measurements yielded the best results and, therefore, this is one preferred method to carry out our invention, although of course less precise results can be obtained using alternative calculations, all of which are encompassed by the invention. However, given CVP is not routinely measured and given its value is generally small in comparison with MABP, the difference (MABP−CVP) may be estimated in several ways such as fraction (e.g. 0.95×MABP) yielding CVRI estimate as indicated by the following formula:

$$CVRI \approx (20*MABP*0.95)/(HR*RR*BSA). \quad (8)$$

CVP may be entirely neglected yielding CVRI estimate as indicated by:

$$CVRI \approx (20*MABP)/(HR*RR*BSA), \quad (9)$$

or CVP may be estimated as constant (e.g. 4 mmHg) yielding CVRI estimate as indicated by:

$$CVRI \approx (20*(MABP-4))/(HR*RR*BSA) \quad (10)$$

Note that in order to estimate the index despite lacking respiratory rate, RR may be estimated through HR e.g. RR=HR/5 at rest, revealing CVRI estimate:

$$CVRI \approx (20*(MABP-CVP))/(HR*(HR/5)*BSA) \quad (11)$$
$$= (100*(MABP-CVP))/(HR^2*BSA)$$

The cardiovascular index for the individual is calculated according to one of the above formulas (6 or 7 or 8 or 9 or 10 or 11) to obtain a number representing the cardio vascular performance reserve which carries diagnostic and severity estimation capabilities. The cardiovascular index is an indication of how much cardio-vascular performance reserve is preserved at the exact moment of measurement—either at rest or under enhance physical activity or under any provocative intervention or during a disease or other medical condition.

The quantitative index provides a momentary diagnostic prediction (at different conditions such as rest and different physical activity intensities) either of being entirely preserved (healthy subject) or indicating reduced cardiovascular performance (heart failure and its severity) or cardiovascular insufficiency (shock) which sometimes called circulatory insufficiency, cardiovascular collapse or circulatory collapse.

The quantitative index enables monitoring cardiovascular dynamics in the short term such as severely ill sepsis patient, myocardial infarction or acute heart failure patient in which severity dynamic evaluation is essential. In these patients monotonous decrease may represent a deterioration which may be the beginnings of an approaching shock even before such deterioration is manifested. It may however indicate circulatory improvement among shock patients, steady state or deterioration.

The quantitative index enables long term cardiovascular performance follow-up indicating improvement, deterioration, steady state or fluctuations over time such as in chronic heart failure patient for example. In these patients identification of the overall trend may enable intervention such as replacing the existing medication or adjust dosing, which may be considered as a step forward towards personalized medication.

Unless otherwise indicated, the CVRI calculation as described herein may be performed by executable code and instructions stored in computer readable medium and running on one or more processor-based systems as described in further details hereinafter. However, state machines, and/or hardware electronic circuits can also be utilized.

Similarly, while certain examples may refer to a health care monitoring systems or data health care devices, electronic medical record as well as other computer or electronic systems can be used, such as, without limitation, a network-enabled personal digital assistant (PDA), a smart phone (e.g., with an operating system and on which a user can install applications) and so on.

Example 1

SV and SVR Measurements are Available

The following is an exemplary method for determining an index for a patient based on SV, SVR, RR and BSA as of formula (6) according to an embodiment of the present invention. The method begins by receiving (or recording depending upon the implementation) the data from an individual that are required to obtain the following parameters: the SV, SVR, RR and BSA. The data from the individual can be measured or obtained by different types of existing healthcare medical devices, or alternatively by a dedicated device configured to measure such data either directly or through indirect estimation and accordingly to calculate the CVRI. The index for the individual is calculated by taking the product SV*SVR divided by RR, BSA and 4 to obtain CVRI a number representing the cardio vascular performance diagnostic and severity estimation capabilities.

Example 2

SV and SVR are Unavailable but Vital Signs are Available

The following is an exemplary method for determining an index for a patient based on MABP, CVP, HR, RR and BSA, as of formulas 7, 8, 9, 10, 11 according to an embodiment of the present invention. The method begins by receiving (or recording depending upon the implementation) the data from an individual that are required to obtain the following parameters: the Arterial Blood Pressure, HR, RR and BSA. The data from the individual can be measured or obtained by different types of existing healthcare medical devices, or alternatively by a dedicated device configured to measure such data and accordingly to calculate the CVRI. The index for the individual is calculated by taking the difference (MABP−CVP) or its estimate as in formulas 7, 8, 9, 10, 11 multiply by 20, divided by the HR, RR and BSA to obtain CVRI a number representing the cardio vascular performance reserve which carries diagnostic and severity estimation capabilities.

The cardiovascular reserve index suggested by the method of the present invention as described by the above examples hereinabove is universally, normalized (regardless of the individual age, body built, health status or gender), quantitative, and can be computed on the basis of easy to measure, available medical measurements in any setting this evaluation is needed (medical office, intensive care facility, hospitals, sport arena, street or battle field triage or self assessment).

An isolated CVRI measurement reveals cardio vascular performance reserve which carry diagnostic and severity prediction. Repeated CVRI measurements over time reveal cardio vascular performance dynamics (which indicates stability, deterioration or improvement of the cardiovascular performance reserve). CVRI may be implemented in continuous monitoring as for patient in shock, severely ill patient, or the patient in risk to deteriorate (e.g., acute heart failure in intensive care unit). CVRI provides long term cardio-vascular performance evaluation as for chronic heart patients on cardiologic follow-up. CVRI provides home monitoring solution (with sampling intervals according the severity) for heart failure patients under tele-medicine care, self assessment, etc.

Figure 6:
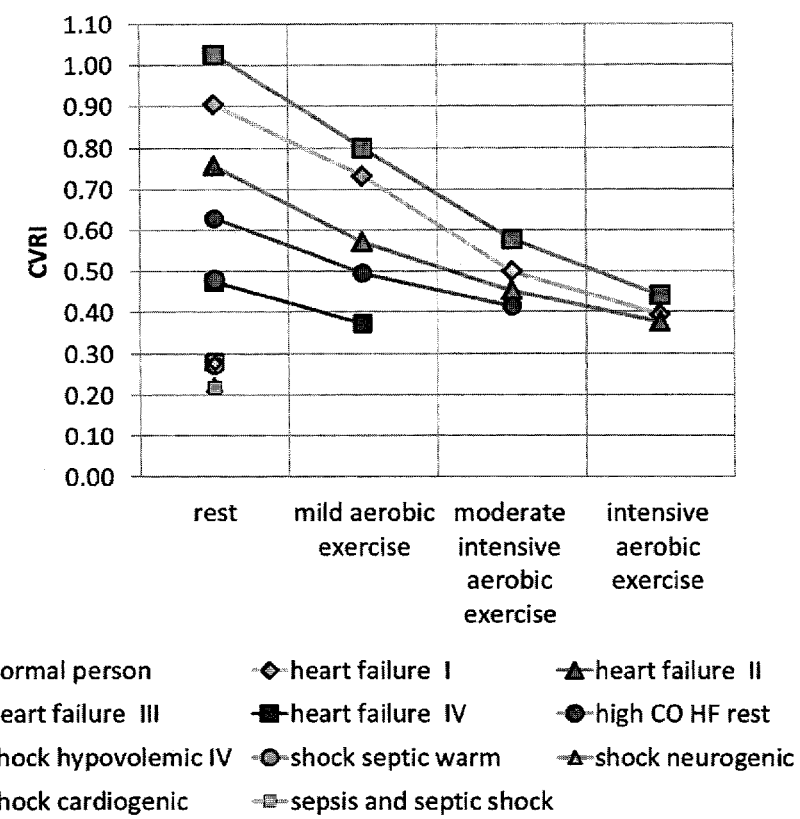
FIG. 6 describes the actual Cardiovascular Reserve Index (CVRI) dependency by physical activity intensity and by heart failure severity, according to an embodiment of the present invention putting the respective average values of each condition for each of the invention formula variables.
Figure 7:
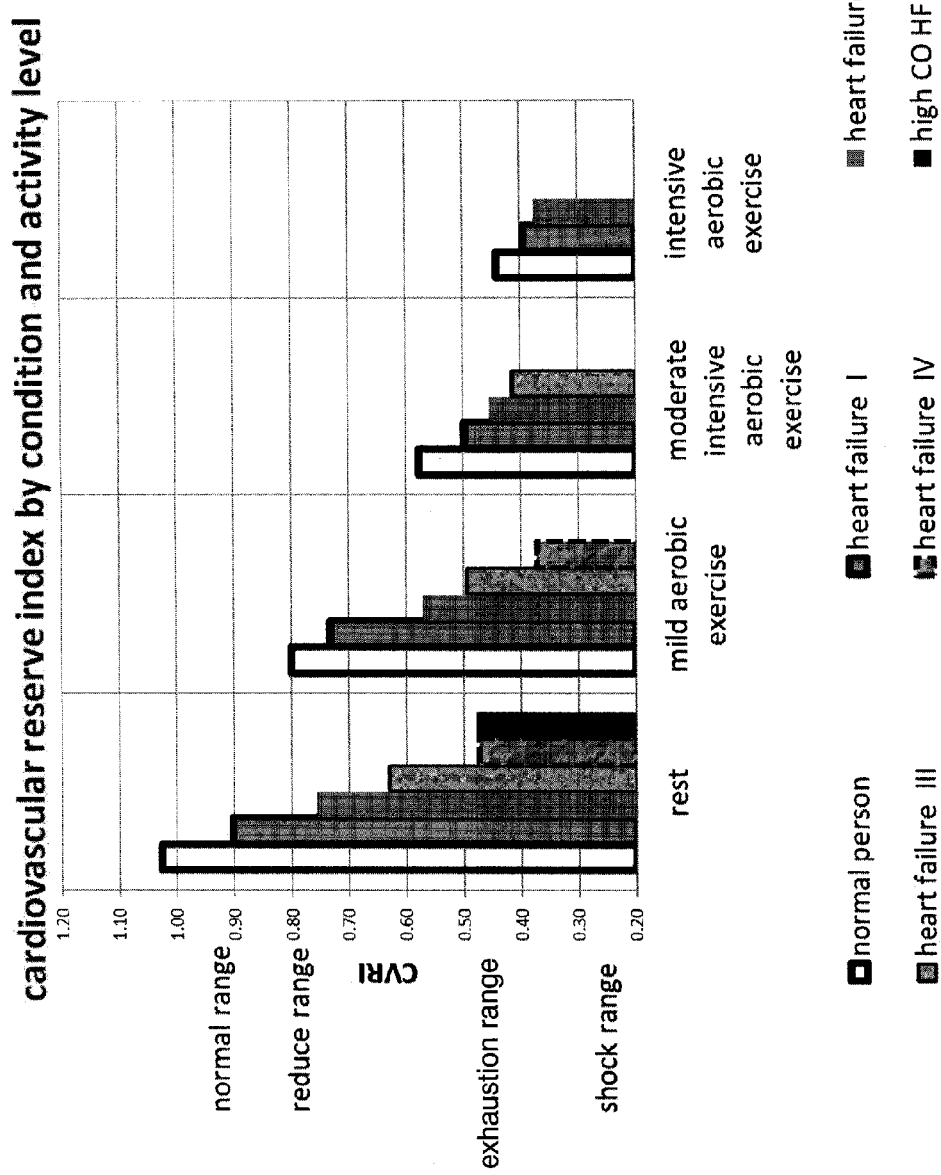
FIG. 7 describes the momentary cardiovascular reserve dependency by physical activity intensity and by heart failure severity, putting the respective average values in the CVRI formula of the invention for each of the invention formula variables.

FIGS. 6 and 7 (bar diagram) describe the actual Cardiovascular Reserve Index (CVRI) dependency by physical activity intensity and by heart failure severity, according to an embodiment of the present invention putting the respective average values of each condition for each of the invention formula variables.

Figure 8:
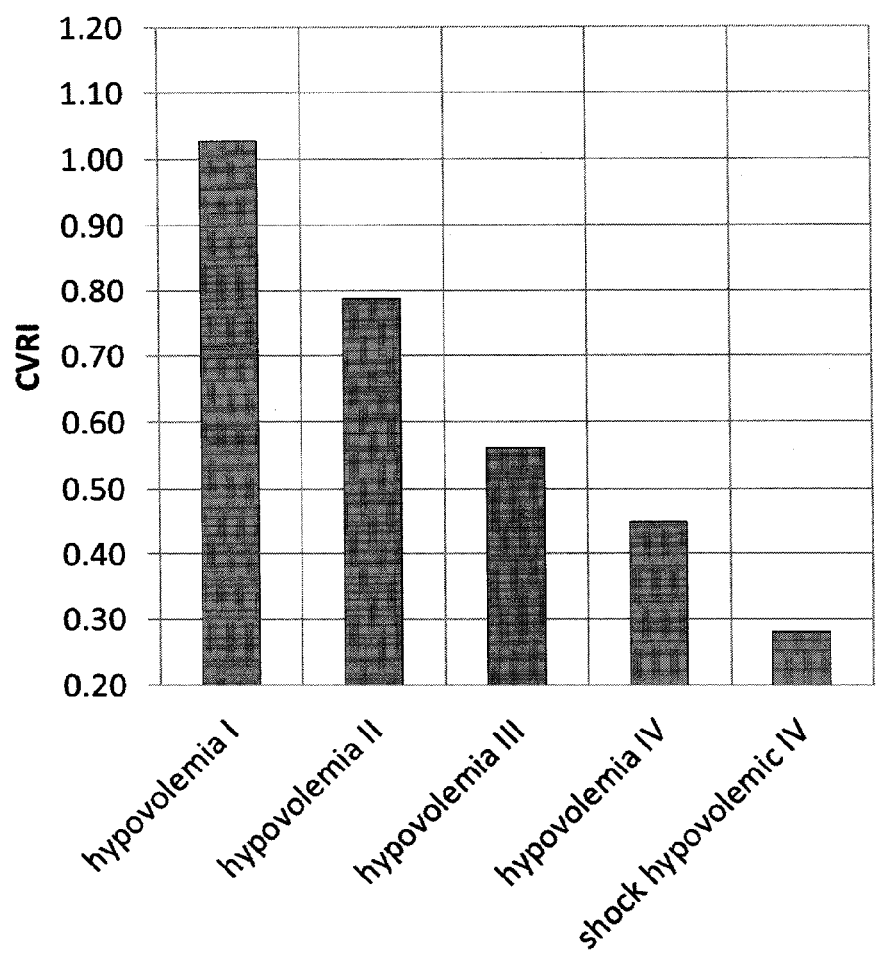
FIG. 8 describes the invention method results estimating momentary cardiovascular reserve dependency by different levels of hypovolemia, according to an embodiment of the present invention putting the respective average values for each of the invention formula variables.

FIG. 8 describes CVRI dependency by different levels of hypovolemia, according to an embodiment of the present invention putting the respective average values for each of the invention formula variables.

Figure 9:
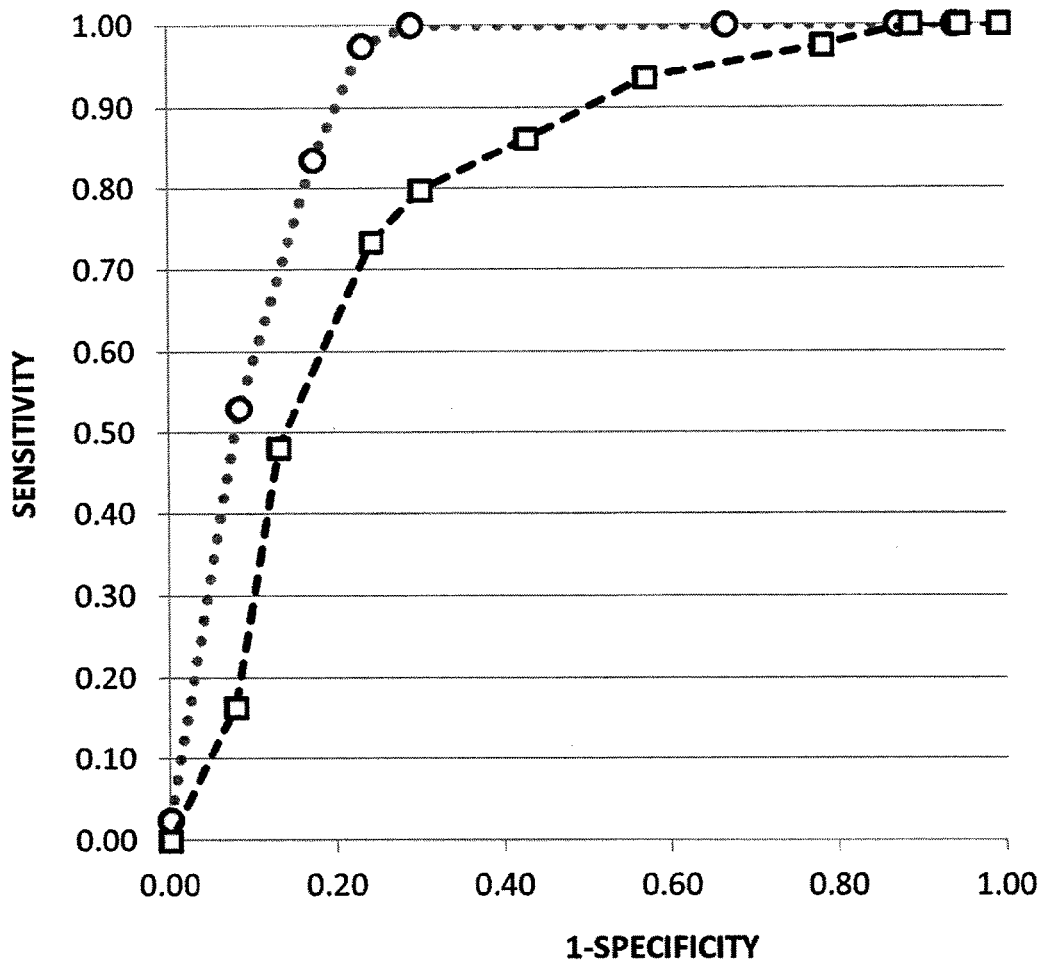
FIG. 9 is a ROC curve for shock prediction by CVRI and by SI.
Figure 10:
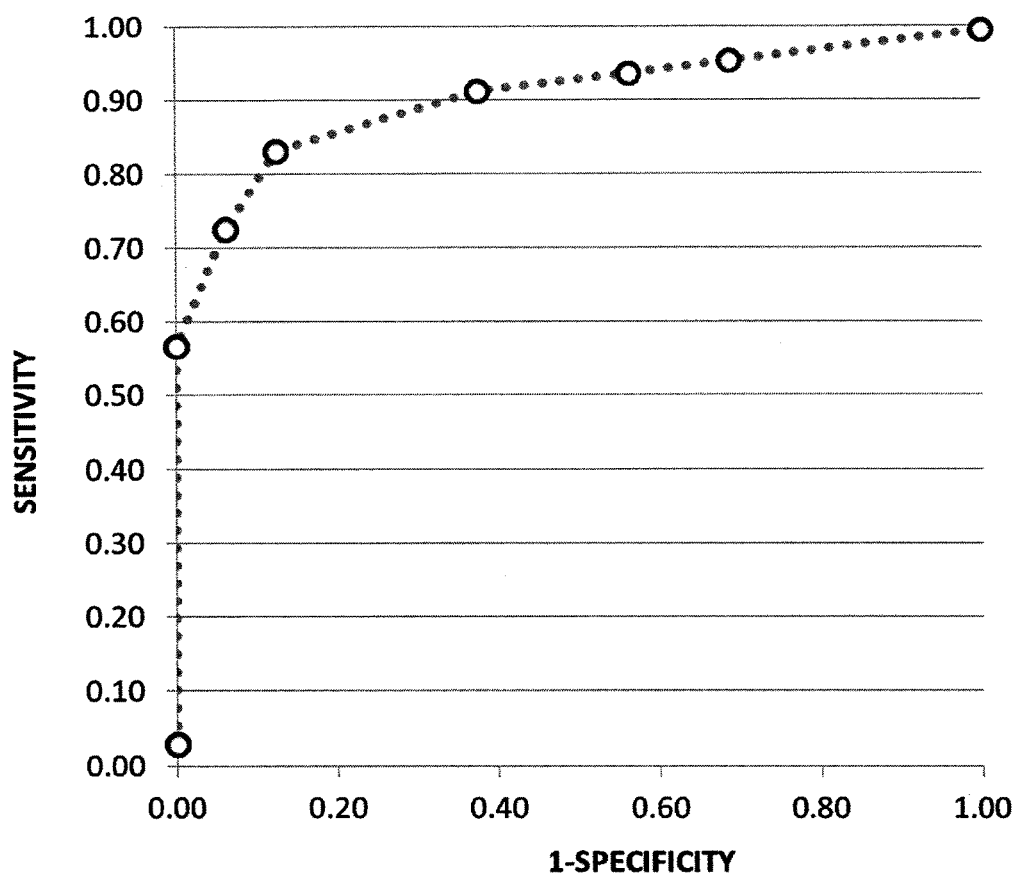
FIG. 10 is a ROC curve for heart failure prediction by CVRI.

Receiver Operating Characteristics ROC is an acceptable method to evaluate diagnostic prediction ("Receiver Operating Characteristics curves and related decision measures: a tutorial", Chemometrics and Intelligent Laboratory Systems, 2006; 80:24-38). As was evident in our cases study (based on case reports published in the literature) CVRI revealed excellent ROC curve for shock prediction which was superior to SI (FIG. 9). We found in our study that CVRI revealed excellent ROC curve for heart failure prediction (FIG. 10).

CONCEPTUAL EMBODIMENTS OF THE INVENTION

Throughout this description the term "medical system" is used to indicate an essentially medical data device/system adapted to analysis physiological measurement data. This term does not imply any particular medical field, construction material or geometry, and the invention is applicable to all suitable medical systems in any field such as intensive care unit, medical office, sport medicine, operation and intervention facilities, mass casualty arena, medical rescue team, remote evaluation, evaluation during training self assessment, inspected assessment or remote inspection, etc. As will be appreciated by the skilled person the medical system can be implemented as a dedicated standalone device or it can be embedded within common devices, such as an ambulatory electrocardiography device.

The below mentioned devices are examples of existing devices which may be adapted to measure CVRI. These devices measure, collect, archive or display all or some of the physiological parameters and vital signs which are utilized in CVRI formula. Utilizing the existing data while accomplishing the missing parameters essential to compute CVRI may indeed enable calculating CVRI. The missing parameters can be accomplished by diverse methods either through adding measuring unit (for example respirometer to measure respiration rate to an automated blood pressure device), keypad interface to input missing measurements (weight and height to compute BSA for example), analyzing existing data to reveal the missing parameter (such as for example analyzing existing ECG data to reveal the respiratory rate) etc.

Holter

A combination of two bolter types: existing ECG bolter and existing blood pressure bolter produce HR and BP but lacks RR, weight and height. RR may be derived by external respiration detector or through ECG analyzing algorithm to detect respiration out of the ECG. Height and weight may be input through an input interface to a processing unit.

Cardio Pulmonary Stress Test

This existing test system is a combination of ECG stress test (ergometry) with existing pulmonary functional test which together produce HR, RR but lacks BP, weight and height. BP may derived by external automatic blood pressure device that export measurements to a processing unit. Height and weight may be input through an input interface to a processing unit.

Ergometry

This existing ECG stress test (ergometry) produces HR, but lacks RR, BP, weight and height. RR may be derived by external respiration detector or through ECG analyzing algorithm to detect respiration out of the ECG. BP may be derived by external automatic blood pressure device that export measurements to a processing unit. Height and weight may be input through an input interface to a processing unit.

Automated Blood Pressure Device

This existing automated BP device produces HR, SBP and DBP but lacks MABP, RR, weight and height. RR may be derived by external respiration detector or best estimated through HR (for example RR≈HR/5 at rest). MABP may be calculated by SBP and DBP. Height and weight may be input through an input interface to a processing unit.

Monitor (Invasive Measurements)

This existing monitoring device detects HR, RR (by different methods, such as (i) impedance, (ii) inspirium/experium detections or measurements, e.g., $CO_2$ measurements through the nose, temperature differences, etc.), MABP (e.g., through arterial line), and CVP (e.g., through central vein line). It may lack anthropometric data such as weight and height which may be input through an input interface to the monitor processing unit.

Monitor (Non-Invasive Measurements)

This existing monitoring device detects HR, RR, NIBP (non invasive blood pressure) which compute MABP through SBP and DBP. It may lack anthropometric data such as weight and height which may be input through an input interface to the monitor processing unit.

Multi-Parametric Tests

Multi-parametric tests, such as Polysomnography (PSG), can also be adapted to calculate the CVRI, if required, by adding complementary measurements such as for example RR.

Figure 11:
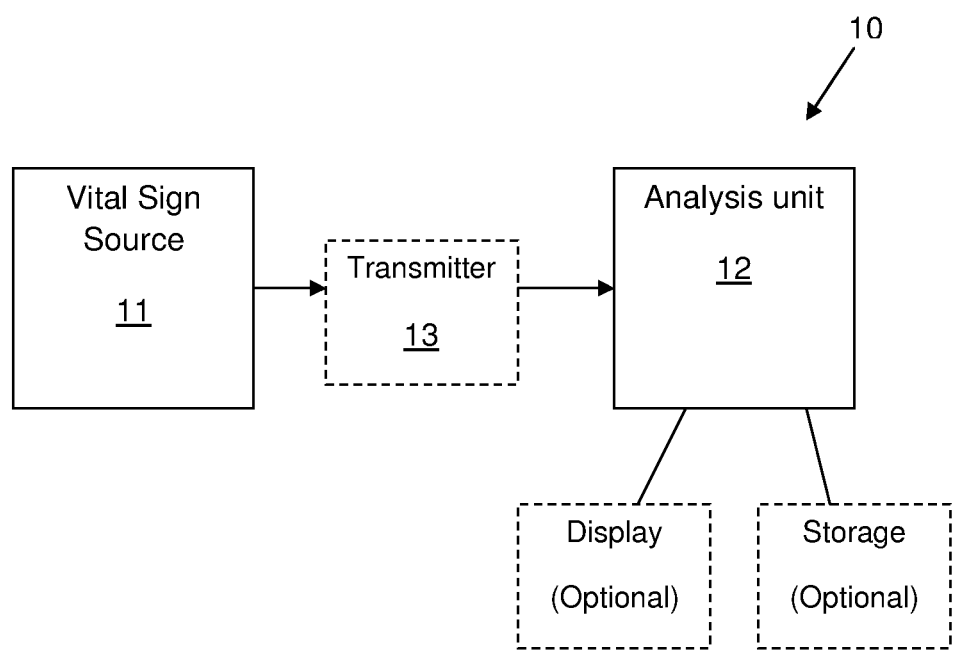
FIG. 11 schematically illustrates a conceptual design of a system for estimating momentary cardiovascular reserve, according to some embodiments of the present invention.

FIG. 11 schematically illustrates a conceptual design of a medical system 10 that can be used in conjunction with the invention for performing the methods discussed above. The illustrated medical system 10 includes a vital sign source 11 and an analysis unit 12 in communication with the vital sign source 11. The system 10 although illustrated with one vital sign source 11 may be expanded to include a plurality of vital sign sources connected to one individual and/or multiple individuals. In at least one exemplary embodiment, an individual would have multiple vital sign sources connected to monitor different vital signs for the system 10. According to some embodiments of the present invention, the system can be designed or configured to handle monitoring of multiple individuals.

The method of the present invention provides a simple quantitative cardiovascular measure which is unique as it can be easily computed either through invasive measurement routinely performed in intensive care facilities or through routine non-invasive vital signs. This measure indicates cardiovascular performance status and may utilized in CVRI derived predictive test as for example for shock prediction and for heart failure prediction.

As will be appreciated by the skilled person the arrangement described in FIG. 11 results in an enhanced medical device, such that the implementation of at least part of the above calculations makes it possible to effectively analyze the patient condition or to provide indication of its cardiovascular status. Exemplary vital sign sources (such as the vital sign source 11 of FIG. 11) may include a vital sign monitor (or sensor) or similar devices as described below:

Implementation within a monitor which displays CVRI numerically (which is physiologically meaningful), and possibly with explicit diagnostic prediction (such as text of "shock" or "heart failure" or "normal" etc.) and trends with or without graphical presentation of CVRI versus time, with explicit text notification (such as "deterioration" or "improvement" over time). Cardiovascular performance quantification and diagnostic prediction are unique and no other method had ever succeeded with.

Figure 12:
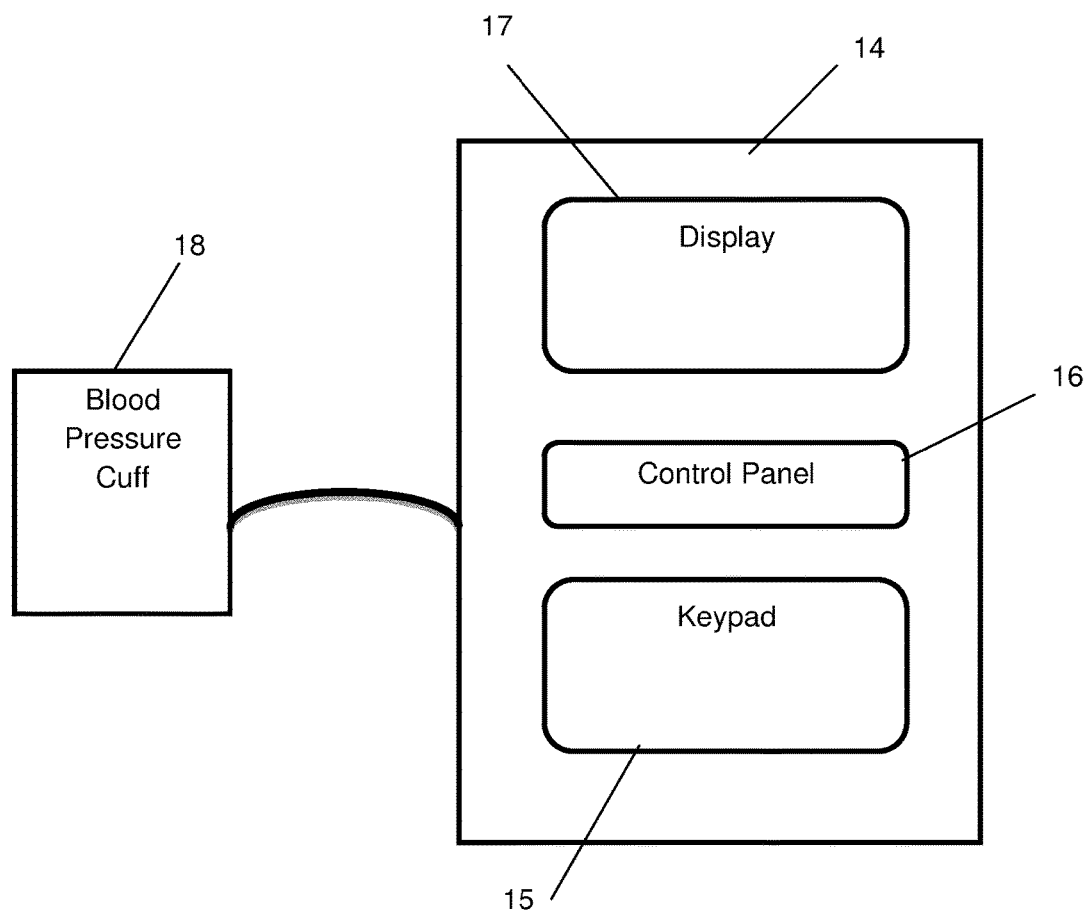
FIG. 12 schematically illustrates an extended automatic non invasive blood pressure device with manual data entry interface, according to an embodiment of the present invention.

FIGS. 12-15 show variations of an ambulatory device that can be used in conjunction with the invention (e.g. for medical offices or self assessment at home). The device illustrated in these figures is particularly convenient because it can be adapted or modified to provide the CVRI without the need to carry out major (or any) alterations in the structure. The device generally indicated by numeral 14 in the FIGS. 12-13 can be a traditional automatic noninvasive blood pressure/pulse measuring device, which comprises a common blood pressure cuff 18 (FIG. 12) and a data entry interface (e.g., a keypad 15, or a touch sensitive screen 17, etc. as shown in FIG. 12) to enter hemodynamic and/or anthropometric related data (such as height, weight) and the respiratory rate (RR), which through embodiment of the invention output CVRI and indicates the cardiovascular status. The device 14 may further comprise a display unit 17, a control panel 16 (which alternatively may be included in the touch sensitive element 17) or other common operating means as shown in FIG. 12.

Figure 13A:
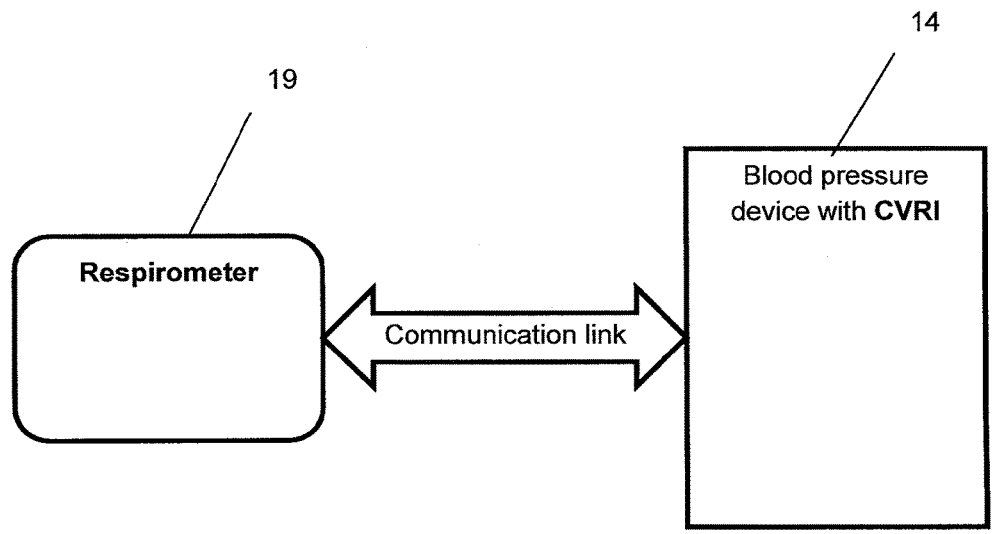
FIG. 13 schematically illustrates the device of FIG. 12 provided with a respiratory rate detection unit.
Figure 13B:
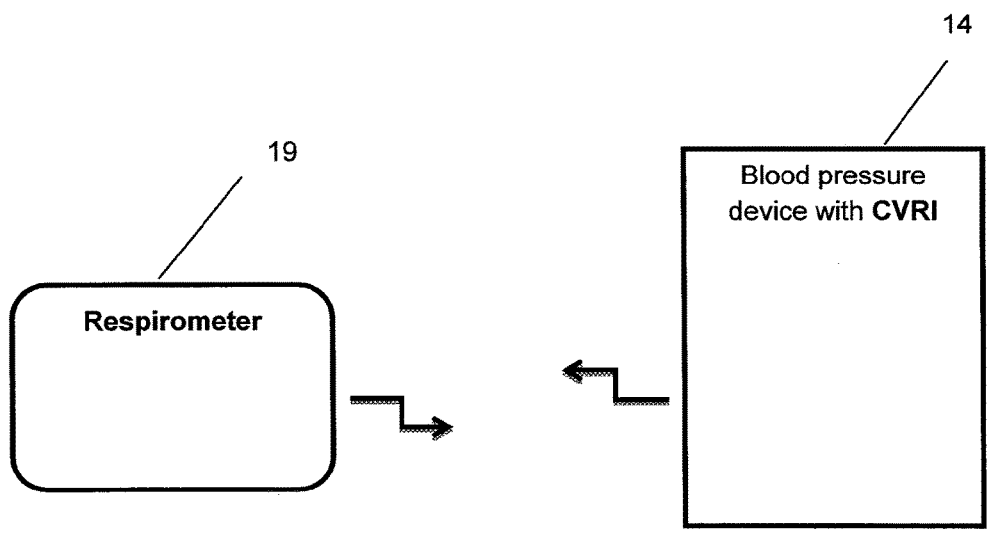

Referring now to FIG. 13, the above device 14 is adapted to communicate also with a respiration rate detection unit counter (e.g., a respirometer 19), either via wired (FIG. 13-A) or wireless (FIG. 13-B) communication link, in order to automatically feeds the respiration rate into the device 14. The wired connection as in FIG. 13-A can also supply power to the respirometer 19.

Figure 14:
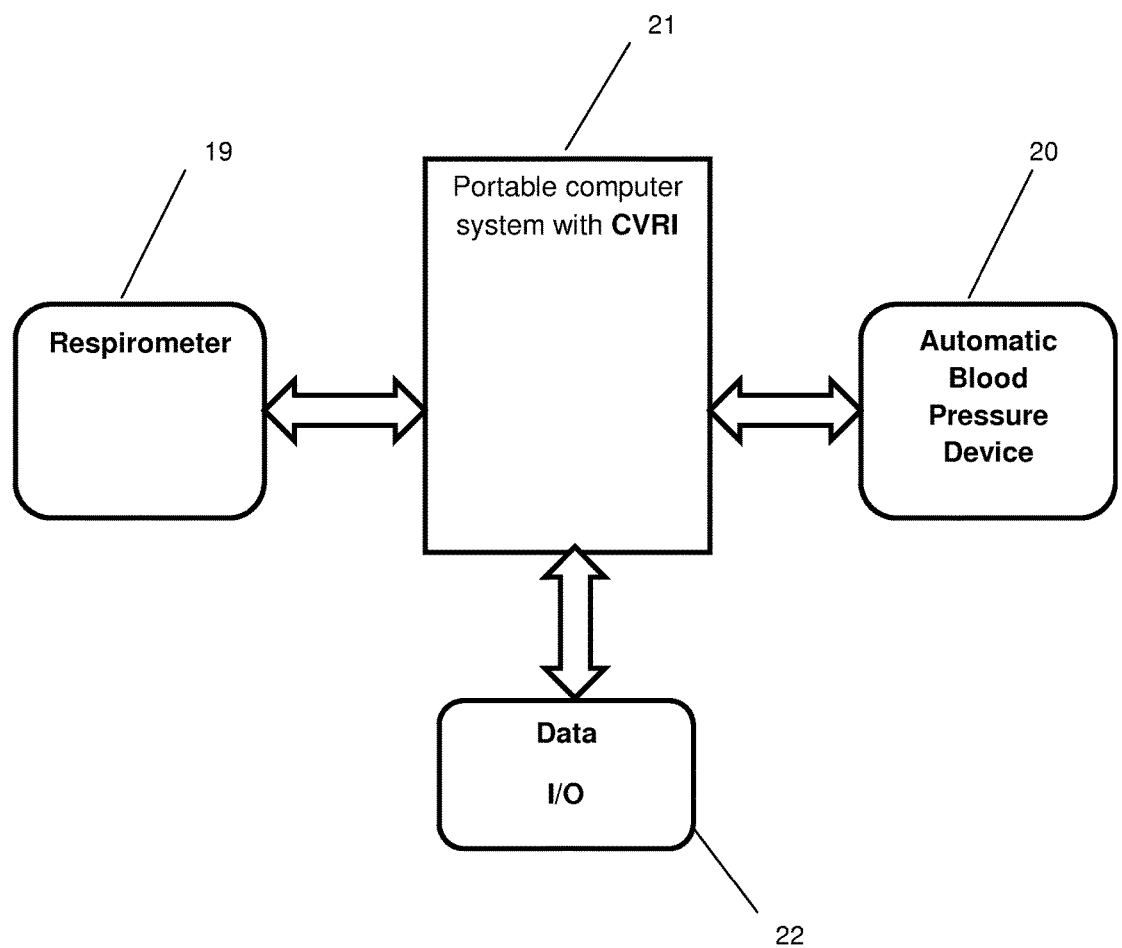
FIG. 14 schematically illustrates the device of FIG. 13 including a central processing unit (such as PDA, notepad etc.)

In FIG. 14, a traditional automatic noninvasive blood pressure/pulse measuring device 20 is shown, which interface into a portable computing device 21 (e.g., a PDA, smart-phone, etc). The portable computing device 21 enables: data entry of anthropometric variables manually, additional data entry such as but not limited to the patient and setting identification, medical history etc. or other relevant data (e.g., via I/O data port 22). The control function may be similar as element 16 in FIG. 12 either directly by the PDA 21 or through 20 or both. In this figure, the portable computing device 21 is in communication with the respirometer 19.

Figure 15:
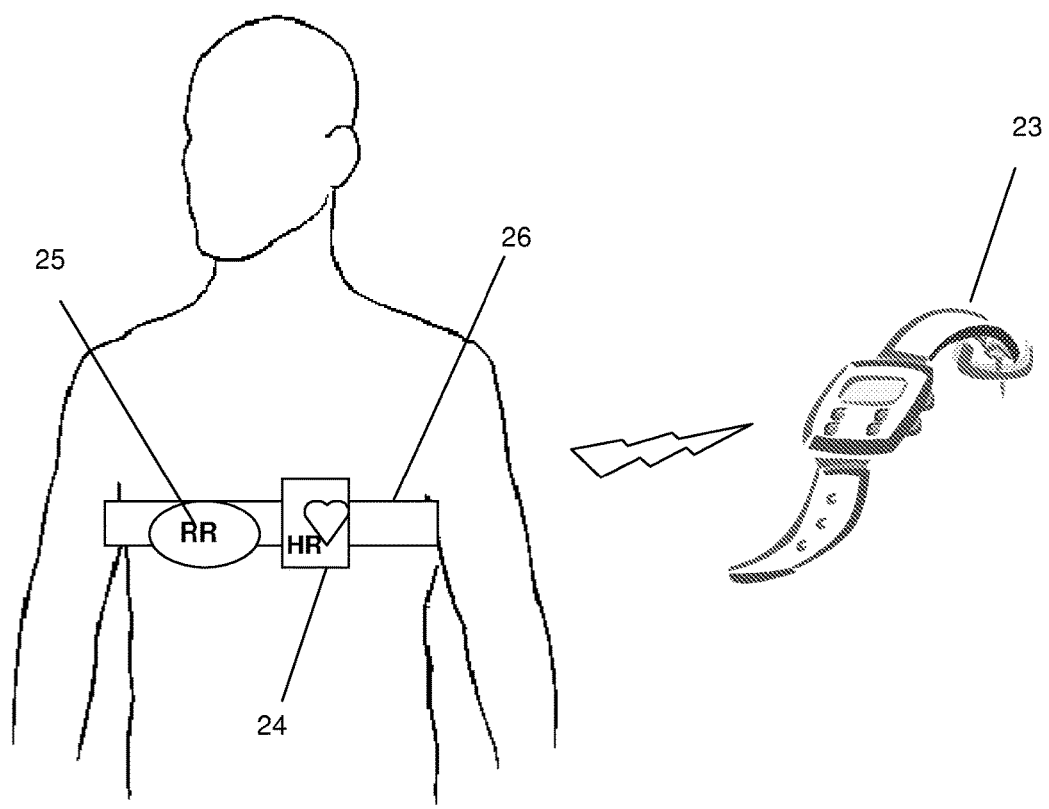
FIG. 15 schematically illustrates an example for implementing the system of the present invention as an extended sport pulse rate device such as "pulse watch" with manual data entry interface and respiratory detection device.

FIG. 15 schematically illustrates an implementation of the CVRI for self assessment during sporting, according to an embodiment of the present invention. In this embodiment, an extended pulse rate sport device 23 which enables input (e.g. manually) of height and weight and the initial blood pressure, in which the respiration rate RR is given either through an existing ECG unit 24 through dedicated analysis or through a dedicated respiratory sensor 25 (e.g. strain gage) embedded in the elastic band of the existing chest strap 26.

Each of the above may include memory, output transmission to a control center, external computer either directly or through a network, archive or printer. Flash memory enables manual transmission and direct viewing through a self operating viewer.

The vital sign monitor will be in communication with an individual where in communication includes having the monitor affixed, attached, implanted, coupled, abutting the individual's tissue, resident in clothing or equipment worn by the individual, and proximate to the individual.

The analysis unit 12 is in communication with the vital sign source 11 through a wired connection or wireless connection such as infrared, radio, Bluetooth, Wi-Fi, etc. where the connection can be continual, intermittent (or on a predetermined schedule), as needed or as permitted by the circumstances. The analysis unit 12 may be a separate component not present on the individual on whom the vital sign source 11 is present or in communication with, for example, to allow remote monitoring of the individual or monitoring during a medical event such as triage, transport, or treatment. In this implementation, the vital sign source 11 is connected to a transmitter (and/or receiver) 13 that allows vital sign data to be communicated to the analysis unit 12 as illustrated in the figure.

Alternatively, the analysis unit 12 may be located on (or proximate to) the individual whom the vital sign source 11 is in communication, and in this implementation an exemplary system for the analysis unit 12 to be configured as part of a given monitoring system that is capable of communicating with a remote user. If the analysis unit 12 is located on the individual, then in at least one exemplary embodiment the analysis unit 12 is connected to a corresponding transmitter (and/or receiver).

The analysis unit 12 processes received vital sign data from the vital sign source 11 and enable anthropometric data entry either directly or through an intermediate component. It may or may not enable identification of the patient and the settings. Depending upon the implementation, the set of vital sign data includes heart rate, respiratory rate and blood pressure to be able to determine the CVRI.

The term blood pressure refers to any measuring method of blood pressure that enable output of MABP, either invasive which compute MABP directly or non invasive which estimate MABP through SBP and DBP.

The analysis unit 12 can be implemented as software on a variety of hardware computing devices including computers and PDAs. The software includes the ability to process the received vital signs signals to provide as an output the desired indicators relating to cardiovascular status and to adjust cut-point level for certain predictive test aims. The software when used to implement the method of the present invention, may include notification/alarm unit to provide notification to the operator/user with an audio notification, a mechanical notification such as vibration, a visual notification including activation of a light(s) or via a display, either as signal, number or text (indicate the exact status such as normal, heart failure (which may or may not indicates its severity) and shock. signal to another entity or device, or any combination of these if predetermined conditions occur or predetermined thresholds are exceed by a vital sign or the indicator. The analysis unit 12 in at least one exemplary embodiment is connected to a storage unit (e.g., a buffer, RAM and disk storage, etc.) for storing data associated with its operation. It may be also transmitted through wired or wireless communication to remote location or from remote location either for telemedicine, central monitoring control or remote archiving.

The invention can take the form of an entirely hardware embodiment, an entirely software embodiment or an embodiment containing both hardware and software elements. In at least one exemplary embodiment, the invention is implemented in software, which includes but is not limited to firmware, resident software, microcode, etc. Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The present invention provides a comprehensive alarm system which carries physiological insight and hence it meets the need of intensive care units regarding the alarm: "to be accurate" and that "it carries intelligence" as such need is well described in the article "Alarms in the intensive care unit: too much of a good thing is dangerous: is it time to add some intelligence to alarms?" by Blum J M et. al., Crit. Care Med. 2010 February; 38(2):451-6. According to the embodiments described hereinabove the system of the present invention provides a quantified cardiovascular performance reserve measure and methods of how to measure it. Moreover, the system of the present invention carries capability of diagnosis prediction (such as normal, heart failure and its severity and shock). Cardiovascular performance quantification and diagnostic prediction are unique and no other method had ever succeeded with.

The terms, "for example", "e.g.", "optionally", as used herein, are intended to be used to introduce non-limiting examples. While certain references are made to certain example system components or services, other components and services can be used as well and/or the example components can be combined into fewer components and/or divided into further components. Moreover, the appearance and terminology as depicted and described herein, are intended to be illustrative and exemplary, and in no way limit the scope of the invention as claimed.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. A method for determining a cardiovascular performance reserve for an individual using a medical system that includes at least one data source and a computerized analysis unit in communication with the at least one data source, the computerized analysis unit employing a processor and a memory, comprising the steps of:
   a. receiving, by the analysis unit from the at least one data source, input physiological data from the individual for obtaining a parameter Z which is or approximates the product of the Stroke Volume (SV) by the Systemic Vascular Resistance (SVR);
   b. providing a value, to the analysis unit from the at least one data source, representing the Respiratory Rate (RR) of said individual;
   c. providing anthropometric data, to the analysis unit from the at least one data source, of said individual for calculating the Body Surface Area (BSA) of said individual;
   d. processing, by the analysis unit, the input physiological data signals to provide a normalized Cardiovascular Reserve Index (CVRI) by using said Z parameter, said RR and said BSA, according to the following formula:

$CVRI=((Z/RR)/(BSA*4))$;

e. outputting said CVRI and estimating the individual's medical condition therefrom; and
   f. outputting a notification of cardiovascular status of the individual based on the CVRI, and prioritizing medical assistance or triage for the individual based on the cardiovascular status notification indicating a heart failure and/or shock condition over other individuals awaiting medical assistance or triage.

2. A method according to claim 1, wherein the input physiological data are measurable hemodynamics-related data of the individual which yield the actual SV and SVR of said individual.

3. A method according to claim 1, wherein Z is approximated by the formula $Z=80*(MABP-CVP)/HR$, wherein the input physiological data are measurable either from non invasive vital signs measurements or from an invasive measurement through an arterial catheter, and wherein these measurements are used for obtaining one or more of the Mean Arterial Blood Pressure (MABP), the Heart Rate (HR), and the Central Venous Pressure (CVP) of said individual.

4. A method according to claim 3, wherein the cardiovascular reserve index is calculated by using the difference (MABP-CVP) or a best estimate of the difference if CVP is not available.

5. A method according to claim 1, wherein the Respiratory Rate (RR) value is provided by measurements using dedicated device(s), calculations from the input physiological data or manually by using a best estimate.

6. A method according to claim 1, wherein outputting a notification of cardiovascular status of the individual comprises using a diagnostic test to quantitatively diagnose heart failure and/or shock, to quantify the severity of the diagnosis and to monitor a severity dynamic, wherein the notification includes quantitative heart failure and/or shock severity information.

7. A method according to claim 1, further comprising providing an indication of cardiovascular status by a trend over time for a cardiovascular dynamics indication, and determining whether medical attention is required for the individual based on the outputted index and the indication.

8. A method according to claim 1, wherein outputting the index includes displaying the index for at least one individual, and creating a graph including the current index and a plurality of past indexes for said individual with or without indication on the trend over time.

9. A system for estimating momentary cardiovascular reserve, comprising:
   a) at least one data source capable of being connected to an individual for obtaining physiological data from said individual, for obtaining anthropometric data related to said individual and for obtaining a value representing the Respiratory Rate (RR) of said individual, wherein said physiological data is used for obtaining a parameter Z which is or approximates the product of the Stroke Volume (SV) by the Systemic Vascular Resistance (SVR), and wherein said anthropometric data is used for a calculation of the Body Surface Area (BSA) of said individual; and b) an analysis unit, employing a processor and a memory, in communication with said at least one data source adapted for processing the data received from said at least one data source, in order to determine an index representing said momentary cardiovascular reserve by calculating a normalized Cardiovascular Reserve Index (CVRI) by using said Z parameter, said RR and said BSA, according to the following formula:

$$CVRI=((Z/RR)/(BSA*4)),$$

wherein the analysis unit is configured to output a notification of cardiovascular status of the individual based on the CVRI, the notification providing heart failure and/or shock information for prioritizing medical assistance or triage for the individual over other individuals awaiting medical assistance or triage.

10. A system according to claim 9, in which the at least one data source includes a vital sign monitor, wherein said vital sign monitor is configured to be in communication with the individual wherein communication includes having said vital sign monitor affixed, attached, implanted, coupled, abutting-tissue of the individual, resident in clothing or equipment worn by said individual, and/or proximate to said individual.

11. A system according to claim 9, in which the analysis unit is in communication with the at least one data source through a wired connection and/or wireless connection.

12. A system according to claim 9, wherein the analysis unit is a separate component not present on the individual on whom the at least one data source is present or in communication with.

13. A system according to claim 9, in which the at least one data source is connected to a transmitter and/or receiver that allows physiological data and anthropometric data to be communicated to the analysis unit, thereby allowing remote monitoring of the individual or monitoring during a medical event such as triage, transport, treatment or telemedicine decision.

14. A system according to claim 9, wherein the analysis unit is configured to provide a diagnostic test to quantitatively diagnose heart failure and/or shock, to quantify the severity of the diagnosis and to monitor a severity dynamic, and the notification of cardiovascular status of the individual includes quantitative heart failure and/or shock severity information.

* * * * *

UNITED STATES PATENT AND TRADEMARK OFFICE
CERTIFICATE OF CORRECTION

| | |
|---|---|
| PATENT NO. | : 9,603,534 B2 |
| APPLICATION NO. | : 14/375355 |
| DATED | : March 28, 2017 |
| INVENTOR(S) | : Uri Gabbay and Ben Zion Bobrovsky |

It is certified that error appears in the above-identified patent and that said Letters Patent is hereby corrected as shown below:

In the Specification

Column 13, Line 64:
Delete "bolter types: existing ECG bolter"
Insert -- holter types: existing ECG holter --

Column 13, Line 65:
Delete "bolter"
Insert -- holter --

Signed and Sealed this
First Day of August, 2017

Joseph Matal
*Performing the Functions and Duties of the*
*Under Secretary of Commerce for Intellectual Property and*
*Director of the United States Patent and Trademark Office*